US006231813B1

(12) United States Patent
Ally et al.

(10) Patent No.: US 6,231,813 B1
(45) Date of Patent: May 15, 2001

(54) GEL LOADING ADAPTER

(75) Inventors: Abdul H. Ally, Gaithersburg, MD (US);
Michael W. Schuette, Vienna, VA (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/154,156

(22) Filed: Sep. 16, 1998

Related U.S. Application Data

(60) Provisional application No. 60/059,031, filed on Sep. 16, 1997.

(51) Int. Cl.[7] .......................... G01N 27/26; G01N 27/447
(52) U.S. Cl. .......................... 422/100; 436/180; 204/456; 204/466; 204/606; 204/616
(58) Field of Search .................. 204/606, 615, 204/616, 618, 619, 456, 466, 467; 422/100; 436/180

(56) References Cited

U.S. PATENT DOCUMENTS

| | | | |
|---|---|---|---|
| 4,304,865 | 12/1981 | O'Brien et al. ........................ 435/240 |
| 4,431,506 | * 2/1984 | Gorman, Jr. et al. ................ 204/619 |
| 4,446,104 | 5/1984 | Hämmerling et al. ................. 422/63 |
| 4,461,328 | 7/1984 | Kenney .................................... 141/67 |
| 4,707,337 | 11/1987 | Jeffs et al. ............................ 422/100 |
| 4,779,467 | 10/1988 | Rainin et al. ...................... 73/864.17 |
| 4,824,642 | 4/1989 | Lyman et al. ......................... 422/100 |
| 4,827,780 | * 5/1989 | Sarrine et al. .................... 204/616 X |
| 5,039,493 | 8/1991 | Oprandy ................................ 422/101 |
| 5,057,281 | 10/1991 | Torti et al. ............................ 422/100 |
| 5,061,449 | 10/1991 | Torti et al. ............................ 422/100 |
| 5,147,522 | * 9/1992 | Sarrine ................................. 204/616 |
| 5,217,593 | * 6/1993 | MacConnell ..................... 204/608 X |
| 5,274,141 | 12/1993 | Nicolaou et al. ..................... 552/220 |
| 5,343,909 | 9/1994 | Goodman ............................. 141/242 |
| 5,494,830 | 2/1996 | Hubscher ............................. 436/518 |
| 5,656,145 | * 8/1997 | Nguyen et al. ...................... 204/618 |
| 5,785,835 | * 7/1998 | Saito et al. .......................... 204/616 |
| 5,800,691 | * 9/1998 | Kozulic ............................ 204/618 X |
| 5,827,745 | 10/1998 | Astle ...................................... 436/54 |
| 5,882,930 | * 3/1999 | Baier ................................ 422/100 X |

\* cited by examiner

Primary Examiner—T. Tung
Assistant Examiner—John S. Starsiak, Jr.
(74) Attorney, Agent, or Firm—Sterne, Kessler, Goldstein & Fox P.L.L.C.

(57) ABSTRACT

An adaptor for a multi-channel pipettor which allows the user to load multiple wells of a gel simultaneously using gel loading tips. The adaptor has apertures at the top which lead to channels which travel the length of the adaptor and exit at the bottom. Gel loading tips, already affixed onto a multi-channel pipettor, are inserted into the apertures at the top of the adaptor and the ends of the tips exit the adaptor through apertures at the bottom of the adaptor. The apertures at the bottom of the adaptor are spaced so that they match the spacing of wells for various gels.

27 Claims, 3 Drawing Sheets

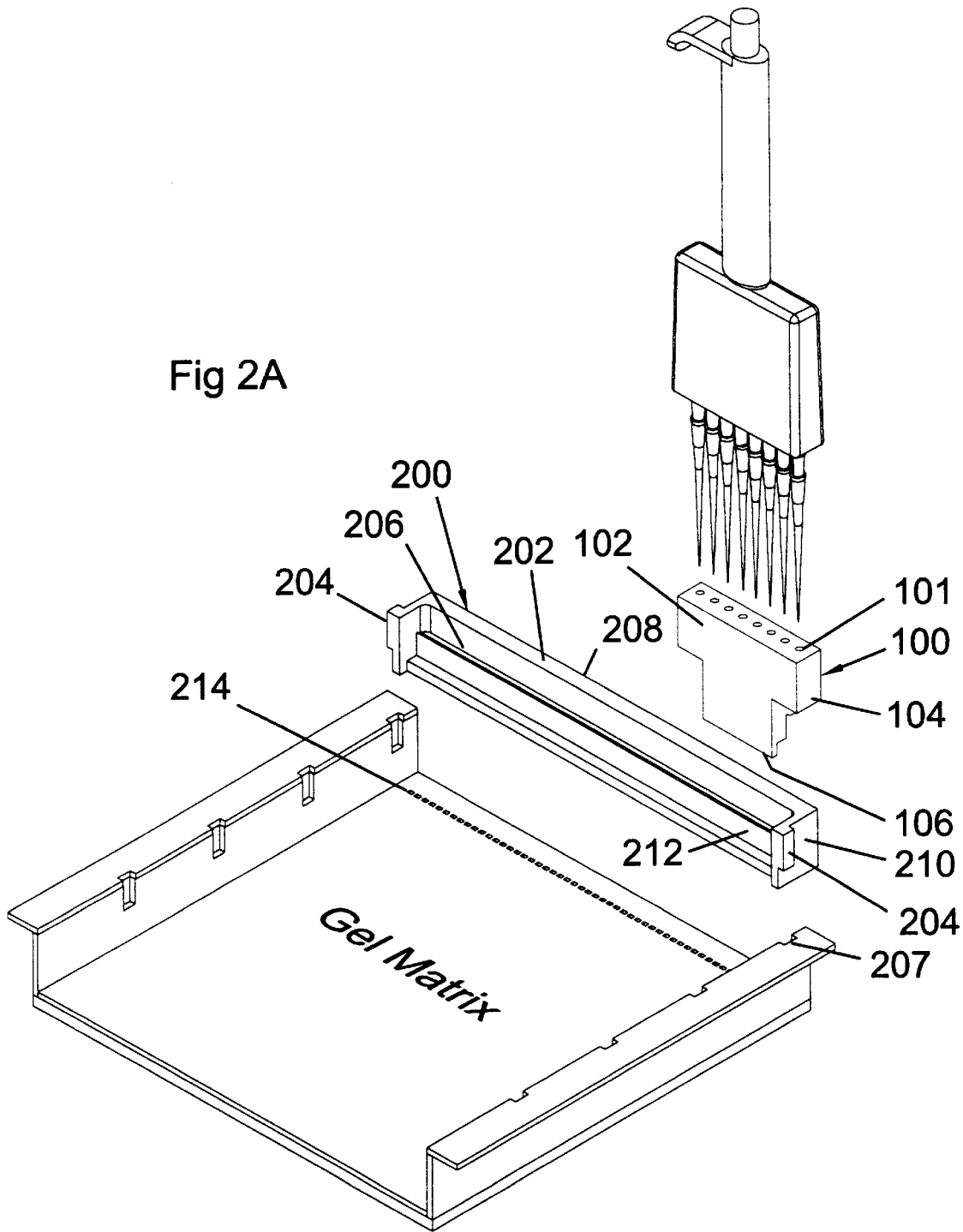

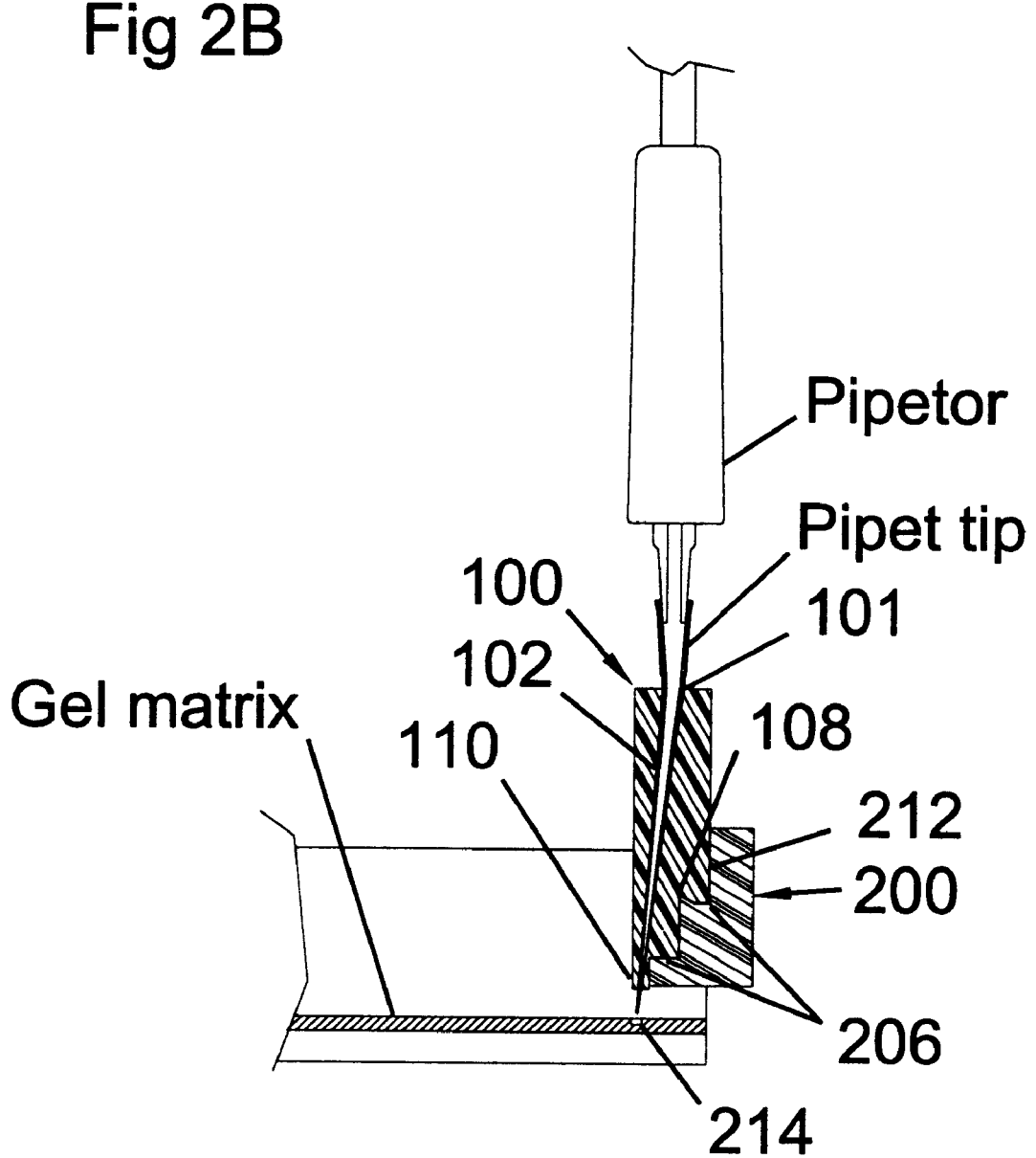

GEL LOADING ADAPTER

This application claims the benefits of earlier filed U.S. Provisional Patent Application No. 60/059,031, filed Sep. 16, 1997.

BACKGROUND OF THE INVENTION

1. Field of the Invention

The present invention relates to an adaptor for multi-channel pipettors which allows for the use of gel-loading tips to simultaneously load multiple wells of a gel.

2. Related Art

Pipettors are used in laboratories to transfer small amounts of liquids (generally 1 ml or less) from one receptacle to another. In recent years the development of multi-channel pipettors, as shown, for example, in U.S. Pat. No. 4,824,642, has allowed for the simultaneous transfer of multiple samples. Because of the fixed spacing between the channels, the transfer of liquids must be made from one set of receptacles to another set of identically spaced receptacles. When it is necessary to transfer liquid from one set of receptacles to another set of receptacles with different spacing it becomes necessary to use a single channel pipettor. The individual transfer of many different samples using a single channel pipettor is a time consuming process.

This can be especially tedious when transferring liquid from receptacles, such as those of a 96 well plate. These plates are heavily used in assays, such as PCR amplification, sequencing, etc. Current technology allows for high volume sample preparation (i.e. the use of multi-channel pipettors to transfer multiple samples from multiple tubes). However, sample analysis in agarose/acrylamide gels still requires individual loading of each sample. Most multi-channel pipettors are configured to match the spacing of the wells on 96 well plates, but this spacing is different than the spacings generally used for the wells of acrylamide and agarose gels. Therefore, the transfer of samples from 96 well plates to acrylamide or agarose gels using a multi-channel pipettor is not possible. These samples must be loaded one at a time into the wells of acrylamide or agarose gels, thereby greatly increasing the time and effort needed to perform research (e.g. sequencing, restriction digest analysis, genetic typing, etc.).

Acrylamide gels are polymerized between two glass plates which are separated by thin spacers on the side. Wells are made by inserting a thin comb at the top of the gel between the two plates before the acrylamide has set. These wells are loaded by pipetting the fluid into the well, being careful not to let the fluid seep into neighboring wells. Agarose gels, on the other hand, are cast in a gel-caster and, again, a comb is placed in the gel to form wells before the agarose is set. Once the agarose is set, it is placed in a gel electrophoresis apparatus filled with buffer and the comb is removed. Depending on the number of wells cast in the agarose, the loading of the samples is tedious and can result in errors if single channel pipetting devices are used.

Standard pipette tips are relatively rigid and wide and are difficult to use when loading acrylamide and agarose gels, which often times have narrow wells. Special tips for loading gels, as shown, for example, in U.S. Pat. No. 4,707,337, are much longer and more flexible than standard pipette tips. They also have a much thinner tip which allows them to load samples into narrow wells much more accurately. These tips are thin enough to fit in between the plates of a vertical gel and, thus, fluid can be delivered directly into the well, rather than from on top of the well with the fluid having to seep in between the two plates. Loading the fluid directly into the well greatly reduces the chances of the fluid seeping into neighboring wells.

In U.S. Pat. No. 5,061,449 and in U.S. Pat. No. 5,057,281, multi-channel pipettors capable of changing the spacing of the channels are described. These multi-channel pipettors contain 6 channels capable of being variably adjusted from being evenly spaced to being unevenly spaced apart. Adjusting these channels every time samples are transferred is very time consuming, especially if one transfers 96 samples from a 96 well plate to other differently spaced receptacles (this requires adjusting the channels 31 times—sixteen times to match the spacing of the receptacles to which the samples are transferred, and 15 times to match the spacing of the 96 well plates). Furthermore, the channels of these adjustable multi-channel pipettors can not be adjusted to match a narrow spacing, such as the spacings between the wells of acrylamide gels. In addition, it is difficult to use gel-loading tips on these pipettors to deliver the samples with any accuracy due to the flexibility and length of the gel-loading tips.

Therefore, there is a need in the art for a device that allows one to simultaneously load multiple wells of a gel in which the spacing of the wells is different (or variable) from the available spacing on the multi-channel pipettors. As the requirement increases for denser loading arrays on gels (vertical, substantially vertical, horizontal, or substantially horizontal) there is a need for devices which can adjust spacing from 96 well microtiter plates to the required spacing in gels. The spacing between the wells of these gels depends on the combs used. Many combs that are commercially available provide variable well size and spacing. Thus, using a single comb, one might have four wells capable of holding only 50 μl of fluid and four wells capable of holding 0.5 ml of fluid. The present invention fulfills this need by allowing one to use multi-channel pipettors currently found in most laboratories to simultaneously load multiple wells of a gel using gel-loading tips. Multi-channel pipettors can cost hundreds of dollars. The prior art requires one to purchase new adjustable multi-channel pipettors, even though one might have a standard multi-channel pipettor at their disposal. Alternatively, the present invention costs a fraction of what a multi-channel pipettor costs. Thus, the present invention provides an inexpensive alternative to the prior art because it does not require the purchase of an expensive adjustable multi-channel pipettor.

SUMMARY OF THE INVENTION

The present invention relates to an adaptor for multi-channel pipettors which allows for the use of gel-loading tips to simultaneously load multiple wells of a gel. In particular, the present invention allows for the loading of vertical, substantially vertical, horizontal, or substantially horizontal gels. The adaptor of the invention may also be used generally in any application involving fluid transfer from a first set of receptacles, containers, wells, tubes, etc., to a second set of differently spaced receptacles, containers, wells, tubes, etc.

In one aspect of the invention, an adaptor useful for transferring multiple fluid samples from a first set of receptacles (wells, tubes, containers, vials, etc.) spaced apart by a first spacing to a second set of receptacles (wells, tubes, containers, vials, etc.) spaced apart by a second evenly or unevenly spaced spacing is provided. The body of the adaptor is defined by a first set of apertures at one end of the body spaced apart by the first spacing and a second set of apertures at the second end of the body, remote from the first end, spaced apart by the second spacing or spacings. The second set of apertures are optionally disposed in an optional lip coupled to the second end of the body. Channels within the body connect the first set of apertures with the second set of apertures.

In another aspect of the invention, a multi-channel pipettor adaptor which includes a means for stabilizing and aligning the adaptor over a gel is provided. The means for stabilizing and aligning can include a base which can be attached to the multi-channel pipettor adaptor. This base has a top and two sides which straddle the gel. One or more guides (e.g. grooves, notches, etc.) are optionally provided in the base which allows the adaptor to be stabilized over a gel such that the second set of apertures are aligned with wells of a gel for loading samples. In one aspect of the invention, the base can slidably receive the adaptor of the invention. In a preferred aspect, the adaptor comprises one or more receiving guides for accepting one or more guides of the base.

In a further aspect of the invention, an assembly useful for transferring multiple fluid samples from a first set of receptacles (wells, tubes, containers, vials, etc.) spaced apart by a first spacing to a second set of receptacles (wells, tubes, containers, vials, etc.) spaced apart by a second evenly or unevenly spaced spacing is provided. This assembly is comprised of the body of the adaptor, which includes a first set of apertures at one end of the body spaced apart by the first spacing and a second set of apertures at the second end of the body, remote from the first end, spaced apart by the second spacing. In this aspect of the invention, channels connect the first set of apertures to the second set of apertures, said channels comprising one or more gel-loading pipette tips inserted into said channels. In a preferred embodiment, such pipette tips are connected to a multichannel pipettor.

In another aspect of the invention, an assembly useful for transferring multiple fluid samples from a first set of receptacles (wells, tubes, containers, vials, etc.) spaced apart by a first spacing to a second set of receptacles (wells, tubes, containers, vials, etc.) spaced apart by a second evenly or unevenly spaced spacing is provided. This assembly is comprised of the body of the adaptor, which includes a first set of apertures at one end of the body spaced apart by the first spacing and a second set of apertures at the second end of the body, remote from the first end, spaced apart by the second spacing, and a multi-channel pipettor inserted into the first set of apertures.

In yet another aspect of the invention, an assembly useful for transferring multiple fluid samples from a first set of receptacles (wells, tubes, containers, vials, etc.) spaced apart by a first spacing to a second set of receptacles (wells, tubes, containers, vials, etc.) spaced apart by a second evenly or unevenly spaced spacing is provided. This assembly is comprised of the body of the adaptor, which includes a first set of apertures at one end of the body spaced apart by the first spacing and a second set of apertures at the second end of the body, remote from the first end, spaced apart by the second spacing, and a base for stabilizing and aligning said adaptor over a gel. In a preferred embodiment, the adaptor/base is coupled such that the second set of apertures are aligned with wells of a gel for sample loading. Preferably, one or more gel-loading pipette tips are inserted into channels connecting the first set of apertures to the second set of apertures in said adaptor.

The adaptor of the invention may be used for any fluid delivery system. While multi-channel pipettors are preferred, automated robots designed to transfer fluid from one receptacle to another may also be used with the present invention. These types of robots are currently available on the market and have multiple components and capabilities. Many of these robots contain both a single channel pipettor and a multi-channel pipettor which can alternately be connected to the robots arm. These pipettors are arranged on a tray along with various arrays of tubes and pipette tips. A computer controls the movements of the robot. The user would program the computer to let it know what types of tubes are being used, which pipettor should be used, and in what order the samples should be transferred. The arm of the robot will attach itself to one of the pipettor attachments (depending on which one it is programmed to attach to). If the robot needs to transfer liquid from one 96 well plate to another 96 well plate it should be programmed to use the multi-channel pipettor. If the robot needs to transfer liquid from 1 ml micro-centrifuge tubes to a 96 well plate, it should be programmed to use the single-channel pipettor.

The adaptor of the invention may be used as a component of the automated robot. The automated robot may be programmed to use the multi-channel pipettor, load gel-loading pipette tips onto the channels of the pipettor, pick up fluid from receptacles (wells, tubes, containers, vials, etc.) spaced apart by a first spacing, attach to the adaptor of the invention, and dispense the fluid into receptacles (wells, tubes, containers, vials, etc.) spaced apart by a second evenly or unevenly spaced spacing. In this way, the robot may be programmed to dispense the fluid into the wells of an agarose or an acrylamide gel. Thus, the adaptor of the invention is particularly suited for use in automated delivery of fluid samples.

In a further aspect of the invention, a method for transferring multiple fluid samples from a first set of receptacles (wells, tubes, containers, vials, etc.) spaced apart by a first spacing to a second set of receptacles (wells, tubes, containers, vials, etc.) spaced apart by a second evenly or unevenly spaced spacing that may be different from the first spacing is provided. This method includes: affixing gel-loading pipette tips onto a multi-channel pipettor; drawing fluid from the first set of receptacles (wells, tubes, containers, vials, etc.) into the gel-loading pipette tips; inserting the gel-loading pipette tips into an adaptor, the adaptor having a first set of apertures configured to interface with the first spacing, and a second set of apertures configured to interface with the second spacing; and dispensing the fluid from the gel-loading pipette tips so that the fluid flows through the adaptor into the second set of receptacles (wells, tubes, containers, vials, etc.). Preferably, the tips extend from the adaptor allowing fluid to flow through the tips within the adaptor thereby avoiding fluid contact with the adaptor. In this manner, the adaptor may be used multiple times without the risk of having fluid from one pipetting contaminating later fluid samples.

In another aspect of the invention, a kit for transferring fluid from one set of receptacles (wells, tubes, containers, vials, etc.) to another set of receptacles (wells, tubes, containers, vials, etc.) which may have different spacing is provided. The kit comprises a carrier being compartmentalized to receive one or more components of the kit. The kit of the invention comprises one or more adaptors, which include a first set of apertures at one end of the body of the adaptor spaced apart by the first spacing and a second set of apertures at the second end of the body of the adaptor, remote from the first end, spaced apart by the second evenly or unevenly spaced spacing. The kit of the invention may further comprise one or more kit components selected from the group consisting of (i) one or more bases for stabilizing and aligning said body over a gel, (ii) one or more gel loading pipette tips, (iii) one or more multi-channel pipettors, and (iv) a gel electrophoresis apparatus (e.g. a vertical, substantially vertical, horizontal, or substantially horizontal gel electrophoresis apparatus).

It is a feature of the multi-channel pipettor adaptor that it can be attached to a multi-channel pipettor. It is a further feature of the adaptor that it can be attached to a base which straddles a vertical, substantially vertical, horizontal or substantially horizontal gel, thereby stabilizing and aligning the adaptor and multi-channel pipettor over the wells of the gel. It is yet a further feature of the adaptor that it can be attached to a vertical or substantially vertical gel, thereby aligning the adaptor and multi-channel pipettor over the wells of the vertical gel.

Another feature of the multi-channel pipettor adaptor is that it can be used together with an automated multi-channel pipettor. Thus, the multi-channel pipettor adaptor can be a component of an automated multi-channel pipettor device.

An advantage of the adaptor is that it allows the user to simultaneously load multiple wells of a gel accurately, thus providing better results and saving time.

A further advantage of the adaptor is that it allows the user to transfer multiple samples of fluid from a first set of receptacles (wells, tubes, vials, containers, etc.) spaced apart by a first spacing to a second set of receptacles (wells, tubes, vials, containers, etc.) which may be spaced apart by a second evenly or unevenly spaced spacing.

BRIEF DESCRIPTION OF THE FIGURES

The present invention is described with reference to the accompanying drawings. In the drawings, like reference numbers indicate identical or functionally similar elements. Additionally, the left-most digit of a reference number identifies the drawing in which the reference number first appears.

FIG. 2A shows a perspective view of one embodiment of a multi-channel pipettor adaptor of the present invention attached to a base to illustrate one embodiment of agarose gel loading; and FIG. 2B shows a side view of the embodiment shown in FIG. 2A.

DETAILED DESCRIPTION OF THE PREFERRED EMBODIMENTS

The present invention is directed generally to an adaptor for multi-channel pipettors that allows the user to simultaneously transfer multiple samples from multiple receptacles (wells, tubes, vials, containers, etc.) having a first spacing to multiple receptacles (wells, tubes, vials, containers, etc.) having a second evenly or unevenly predetermined spaced spacing. In particular, the present invention has utility in transferring samples from sample holders to wells of a gel used in gel electrophoresis. Such gels are used to separate and/or analyze proteins or nucleic acid molecules (e.g. DNA or RNA) or other biological materials. Typically, agarose or acrylamide gels are used in such procedures. In accordance with the invention, gel loading tips connected to a multi-channel pipettor are used to take up fluid from a number (two or more) of receptacles (wells, vials, tubes, containers, etc.) wherein the receptacles have a certain predetermined spacing. The adaptor of the invention provides a means of transferring the fluid to a second set of receptacles which may have a different spacing. Thus, the adaptor of the invention is used to either expand (enlarge) or contract (make smaller) the spacing needed for fluid transfer between the first set of receptacles to the second set of receptacles. Alternatively, the adaptor of the invention may be used without loading tips. In this embodiment, the multi-channel pipettor is connected to the adaptor and fluid is taken-up directly into and expelled directly from the adaptor.

The adaptor of the invention may be used for any fluid delivery system. While pipettors are preferred, automated fluid delivery systems, such as robots equipped with various pipettors and multi-tube arrays, can also be used with the adaptor of the present invention. In this embodiment, the adaptor would be a component of the automated fluid delivery systems. For example, the robot secures its arm to a multi-channel pipettor, loads gel-loading pipette tips onto the channels of the multi-channel pipettor, takes up fluid into the pipette tips from a first set of receptacles (wells, tubes, containers, vials, etc.) spaced apart by a first spacing, and then secures the multi-channel pipettor onto the adaptor of the invention. Having done this, the robot is able to transfer the samples to other receptacles (wells, tubes, containers, vials, etc.) spaced apart by a second evenly or unevenly spaced spacing. Thus, the adaptor of the invention is particularly suited for use in automation.

Figure 1A:
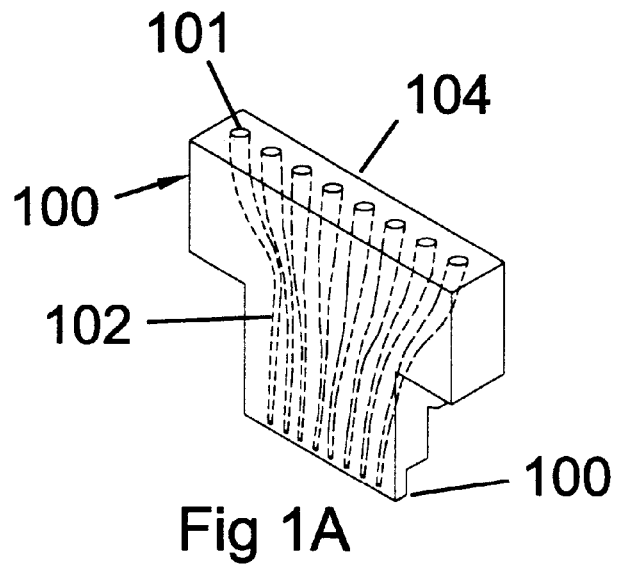
FIG. 1A shows a perspective view of one embodiment of a multi-channel pipettor adaptor of the present invention.

Turning now to FIG. 1A, an adaptor 100 having a body 104 is shown. Body 104 can be made from any of a variety of materials including, but not limited to, metal, glass, ceramic and plastic. Suitable plastics include acrylic compounds such as polypropylene, polycarbonate and polyester resin that can be used to form body 104 by injection or vacuum molding techniques. Body 104 can also be manufactured by welding a metal, such as aluminum, together to form the base. Another technique would be to drill holes into a metal block or other material. Also, glass or ceramics can be used to form the body by injection molding. Other techniques and materials known to the skilled artisan can be used to form body 104. The shape shown in the figures for body 104 is exemplary in nature, and it should be understood that the present invention is not limited to the illustrated shape. For example, body 104 can have a rectangular, trapezoidal, or other suitable shape.

Figure 1B:
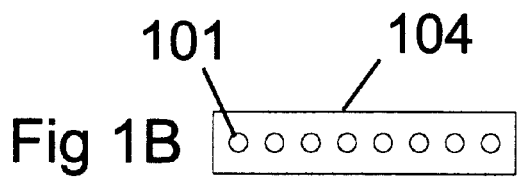
FIG. 1B shows a top view of the embodiment shown in FIG. 1A.
Figure 1C:
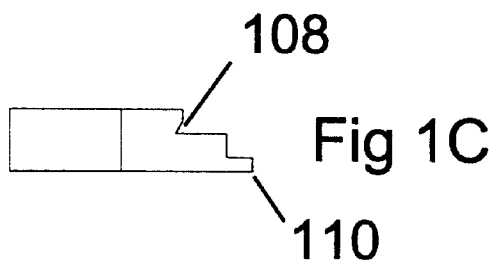
FIG. 1C shows a side view of the embodiment shown in FIG. 1A.
Figure 1D:
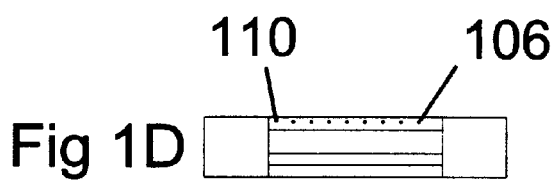
FIG. 1D shows a bottom view of the embodiment shown in FIG. 1A.

As shown in FIG. 1B, an adaptor 100 includes apertures 101 at the top of body 104. The present invention is not limited to the number of apertures 101 shown in the figures, but preferably includes at least two, more preferably two to one hundred, most preferably eight apertures. Apertures 101 may have any spacing and any arrangement depending on the need. For example, the apertures may be in a single row or multiple rows, arranged in a circle, square, rectangle, triangle, oval, etc. configuration. By way of illustration, the apertures may be configured to have the same spacing and configuration as a 96 well plate. Preferred spacing ranges from about 1 mm to 1000 cm, about 2 mm to 100 cm, about 5 mm to 10 cm, and about 5 mm to 10 mm. To match the spacing of the air channels on multi-channel pipettors, the spacing may range from about 7 to 11 mm and preferably about 9 mm. Apertures 101 are the starting points of channels 102, as shown in FIG. 1A. Channels 102 run the length of body 104 and exit through the same number of apertures 106 in a optional small lip 110 at the bottom of body 104, as shown in FIG. 1D. Preferred spacing of apertures 106 may range from about 0.1 mm to 2000 cm, about 1 mm to 200 cm, about 2 mm to 20 cm, and about 2 mm to 10 mm. FIG. 1C shows a side view of 104 and illustrates a receiving lip 108 and small lip 110.

Exemplary dimensions of one embodiment of body 104 are as follows. The height of body 104 may be about 1 inch to 250 feet, more preferably about 2 to 3 inches, most preferably about 2.25 inches. The width of the top of body 104 may be about 1 inch to 350 feet, more preferably about 2 to 4 inches, most preferably about 2.8 inches. The width at the bottom of body 104 may be about 1 inch to 250 feet, more preferably about 1 to 3 inches, most preferably about 1.9 inches. Body 104 may be about 0.1 inches to 100 feet thick, more preferably about 0.3 to 1 inch thick, most preferably about 0.5 inches thick. Receiving lip 108 may be about 0.1 inches to 50 feet wide, more preferably about 0.2 to 0.5 inches wide, most preferably about 0.3 inches wide, and may be about 0.1 inch to 20 feet in height, more preferably about 0.1 to 0.2 inches in height. Small lip 110 may be about 0.02 inch to 20 feet wide at the top, more preferably about 0.05 to 0.2 inches wide, most preferably about 0.1 inch wide, and may be about 0.1 inch to 70 feet wide at the bottom, more preferably about 0.3 to 0.7 mm wide, most preferably about 0.5 mm wide. The height of small lip 110 may be about 0.05 inch to 20 feet tall, more preferably about 0.1 to 0.2 inches tall.

In one embodiment of the invention, gel-loading pipette tips are affixed onto a multi-channel pipettor and fluid is drawn into them. The ends of the gel-loading pipette tips are inserted into apertures 101 at the top of body 104. The tips are then threaded through channels 102 and exit body 104 through apertures 106 at the bottom of body 104. The spacing of apertures 101 is preferably different from the spacing of apertures 106. Apertures 101 are preferably evenly spaced about 7 to 11 mm apart, more preferably about 9 mm apart. Apertures 106 may be more narrowly spaced. Alternatively, apertures 106 may be wider and evenly spaced, or wider and variably spaced. Therefore, channels 102 may be configured as shown in FIG. 1A so that they curve inward toward the middle of body 104 to accommodate the difference in spacing between apertures 101 and apertures 106. Channels 102 alternatively may be configured so that they curve outwards towards the sides of body 104.

Channels 102 are also preferably configured so that each of the gel-loading pipette tips protrudes from small lip 110 the same distance. The tips toward the outer sides of body 104 travel the farthest, and therefore would protrude the least from small lip 110. The tips in the middle of body 104 travel the least, and would protrude the most from small lip 110. Thus, channels 102 toward the middle of body 104 must bend or increase the distance traveled by the pipette tips so that when the pipette tips protrude from small lip 110 they are even with the pipette tips toward the outer sides of body 104.

Adaptor 100 is placed into the buffer reservoir of a vertical or substantially vertical gel box. Small lip 110 is placed between the two plates of a vertical or substantially vertical acrylamide gel and apertures 106 are then aligned correctly with the wells in the acrylamide gel. Gel-loading pipette tips affixed on a multi-channel pipettor are threaded through channels 102 and exit body 104 through apertures 106. The fluid is then dispensed from the tips, and adaptor 100 is removed from the buffer reservoir of the gel box. Adaptor 100 can be removed manually from the multi-channel pipettor and the tips can then be ejected and disposed of.

In another aspect of the present invention, a means for stabilizing and aligning the adaptor over a vertical, substantially vertical, horizontal or substantially horizontal gel is provided. The means for stabilizing and aligning can include, for example, a base as described below with respect to FIGS. 2A and 2B. The means for stabilizing and aligning the adaptor over a gel can also include a electrophoresis apparatus specially made to allow for the adaptor to be attached to it. Alternatively, a special attachment for the electrophoresis apparatus could be used to stabilize and align the adaptor over a gel. The means for stabilizing and aligning the adaptor over a gel can also include manually positioning the adaptor over the gel.

Turning now to FIG. 2A, the multi-channel pipettor adaptor 100 of the present invention is shown along with a base 200. Base 200 can be made from any of a variety of materials including, but not limited to, metal, glass, ceramic and plastic. Suitable plastics include acrylic compounds such as polypropylene, polycarbonate and polyester resin that can be used to form base 200 by injection or vacuum molding techniques. Base 200 can also be manufactured by welding a metal, such as aluminum, together to form the base. Also, glass or ceramics can be used to form base 200 by injection molding. Other techniques and materials known to the skilled artisan can be used to form base 200. The shape shown in the figure for base 200 is exemplary in nature, and it should be understood that the present invention is not limited to the illustrated shape. Base 200 is composed of a body 202 with a back 208, two sides 210, two horizontal support members 204, and an angled ledge 212. The shape shown in the figures for body 202, horizontal support members 204, back 208, side 210, and angled ledge 212 are exemplary in nature, and it should be understood that the present invention is not limited to the illustrated shape. For example, body 202 can have a triangular, rectangular, trapezoidal, or other suitable shape. Horizontal legs 204 may have a semi cylindrical, rectangular, or other suitable shape.

Angled ledge 212 has one or more grooves 206 which run the length of the hypotenuse of angled ledge 212. FIG. 2B shows a side view of base 200 and body 104 and illustrates how the two are secured to one another. The body 104 is secured to the base 200 by inserting receiving lip 108 into groove 206. Optionally, angled ledge 212 may have multiple grooves to accept multiple lips on a multi-channel pipettor adaptor.

Turning back to FIG. 2A, base 200 is positioned over a horizontal gel by inserting horizontal support members 204 into the receiving channels 207 on the side of a horizontal gel caster which has already been submerged in buffer in the buffer chamber of a gel electrophoresis apparatus. Body 104 is then attached to base 200 by inserting receiving lip 108 into groove 206 with small lip 110 hanging over the side of body 202. Body 104 is then centered on base 200 by sliding the body 104 so that the apertures 106 are aligned with the wells 214 of the gel. In a manner similar to that described above, gel loading tips are affixed onto a multi-channel pipettor and fluid is drawn into them. The tips are then inserted into apertures 101 on top of body 104. The tips are threaded through channels 102 and exit body 104 through apertures 106 at the bottom of body 104. The fluid in the tips is then dispensed into the wells 214. The multi-channel pipettor is then removed from body 104 and the gel loading tips are ejected and disposed of. Body 104 may then either be removed from base 200 or slid further down the base 200 so that subsequent wells may be loaded with samples.

While the foregoing invention has been described in some detail for purposes of clarity and understanding, it will be appreciated by one skilled in the art from a reading of this disclosure that various changes in form and detail can be made without departing from the true scope ofthe invention and appended claims. All publications, patent applications and patents cited herein are fully incorporated by reference herein in their entirety.

What is claimed is:

1. An adaptor useful for transferring multiple fluid samples from a first set of receptacles to a second set of receptacles, comprising:

a body, said body defining
    a first set of apertures at one end of said body, said first set of apertures spaced apart by a first spacing,
    a second set of apertures at a second end of said body remote from said first end, said second set of apertures spaced apart by a second spacing, wherein said second spacing is different than said first spacing, and
    channels within said body connecting said first set of apertures with said second set of apertures.

2. An adaptor as defined in claim 1, wherein said body comprises plastic.

3. An adaptor as defined in claim 1,
wherein said second end of said body is a lip, and said second set of apertures is disposed in said lip.

4. An adaptor as defined in claim 3,
wherein said adaptor has sides substantially parallel to said channels, and one or more receiving lips formed in a side of said body, wherein said receiving lips are used to guide the adaptor.

5. An adaptor as defined in claim 1, wherein the second set of apertures are evenly spaced.

6. An adaptor as defined in claim 1, wherein the second set of apertures are unevenly spaced.

7. An adaptor as defined in claim 1, further comprising:
a means, coupled to said body, for stabilizing and aligning said body over a vertical, substantially vertical, horizontal, or substantially horizontal gel.

8. An adaptor as defined in claim 7, wherein said means for stabilizing and aligning comprises:
a base having a body with a back, two sides, and two horizontal support members.

9. An adaptor as defined in claim 8, wherein said base further comprises:
an angled ledge, extending downwards and outwards from said back, comprising one or more grooves for slidably guiding said body.

10. An assembly useful for transferring multiple fluid samples from a first set of receptacles to a second set of receptacles, comprising:

a body, said body defining
    a first set of apertures at one end of said body, said first set of apertures spaced apart by a first spacing,
    a second set of apertures at a second end of said body remote from said first end, said second set of apertures spaced apart by a second spacing, wherein said second spacing is different than said first spacing, and
    channels within said body connecting said first set of apertures with said second set of apertures; and
gel-loading pipette tips inserted into said channels.

11. An assembly as defined in claim 10, wherein said second set of apertures transfers fluid to wells of an electrophoresis gel.

12. An assembly as defined in claim 11, further comprising:
an automated fluid transferring device for transferring fluid from the first set of receptacles to said wells of an electrophoresis gel.

13. An assembly as defined in claim 10, further comprising:
a multi-channel pipettor attached to said gel-loading pipette tips.

14. An assembly useful for transferring multiple fluid samples from a first set of receptacles to a second set of receptacles, comprising:

a body, said body defining
    a first set of apertures at one end of said body, said first set of apertures spaced apart by a first spacing,
    a second set of apertures at a second end of said body remote from said first end, said second set of apertures spaced apart by a second spacing, wherein said second spacing is different than said first spacing, and
    channels within said body connecting said first set of apertures with said second set of apertures;
a base coupled to said body for stabilizing and aligning said body over a vertical, substantially vertical, horizontal, or substantially horizontal gel; and
gel-loading pipette tips inserted into said channels.

15. An assembly as defined in claim 14, further comprising:
a multi-channel pipettor attached to said gel-loading pipette tips.

16. An assembly useful for transferring multiple fluid samples from a first set of receptacles to a second set of receptacles, comprising:

a body, said body defining
    a first set of apertures at one end of said body, said first set of apertures spaced apart by a first spacing,
    a second set of apertures at a second end of said body remote from said first end, said second set of apertures spaced apart by a second spacing, wherein said second spacing is different than said first spacing, and
    channels within said body connecting said first set of apertures with said second set of apertures; and
a multi-channel pipettor inserted into said channels.

17. An assembly as defined in claim 16, further comprising:
a base coupled to said body for stabilizing and aligning said body over a vertical, substantially vertical, horizontal, or substantially horizontal gel.

18. A method for transferring multiple fluid samples from a first set of receptacles spaced apart by a first spacing to a second set of receptacles spaced apart by a second spacing, comprising:

(a) affixing gel-loading pipette tips onto a multi-channel pipettor;
(b) drawing fluid from the first set receptacles into the gel-loading pipette tips;
(c) inserting the gel-loading pipette tips into an adaptor, wherein the adaptor has channels leading from at least two apertures at the top of the adaptor, configured to interface with the first spacing, to a second set of apertures at the bottom of the adaptor, configured to interface with the second spacing;
(d) threading the gel-loading pipette tips through the channels so that they extend from the apertures at the bottom of the adaptor; and (e) dispensing the fluid from the gel-loading pipette tips so that fluid flows through the adaptor into the second set of receptacles.

19. A method for transferring multiple fluid samples from a first set of receptacles to a second set of receptacles, comprising:
   (a) inserting the channels of a multi-channel pipettor into an adaptor wherein the adaptor has channels leading from at least two apertures at the top of the adaptor, spaced apart by a first spacing, to a second set of apertures at the bottom of the adaptor, spaced apart by a second spacing, wherein said second spacing is different than said first spacing;
   (b) drawing fluid from the first set of receptacles into the adaptors channels; and
   (c) dispensing the fluid from the adaptors channels so that fluid flows through the adaptor into the second set of receptacles.

20. A kit for transferring fluid from one set of receptacles to another set of receptacles which comprises one or more containers wherein:
   a first container contains an assembly useful for transferring multiple fluid samples for a first set of receptacles spaced apart by a first spacing to a second set of receptacles spaced apart by a second spacing, the assembly comprising
      a body having channels leading from at least two apertures at the top of the multi-channel pipettor adaptor, having a first spacing, configured to mate with the air channels of a multi-channel pipettor, to a second set of apertures at the bottom of the multi-channel pipettor adaptor, having a second spacing, wherein said second spacing is different than said first spacing, and
      a base for stabilizing and aligning said body over a gel; and
   a second container contains gel-loading pipette tips.

21. The kit of claim 20, wherein said second container further contains a multi-channel pipettor.

22. The kit of claim 20, wherein said second container further contains a gel-electrophoresis apparatus.

23. The kit of claim 20, wherein said kit further comprises:
   a third container which contains a multi-channel pipettor.

24. The kit of claim 23, wherein said kit further comprises:
   a fourth container which contains a gel-electrophoresis apparatus.

25. The kit of claim 20, wherein said kit further comprises:
   a third container which contains a gel-electrophoresis apparatus.

26. The kit of claim 20, wherein said second container contains a multi-channel pipettor.

27. A kit for transferring fluid from one set of receptacles to another set of receptacles which comprises one or more containers wherein:
   a first container contains an assembly useful for transferring multiple fluid samples from a first set of receptacles spaced apart by a first spacing to a second set of receptacles spaced apart by a second spacing, the assembly comprising
      a body having channels leading from at least two apertures at the top of the multi-channel pipettor adaptor, having a first spacing, configured to mate with the air channels of a multi-channel pipettor, to a second set of apertures at the bottom of the multi-channel pipettor adaptor, having a second spacing, wherein said second spacing is different than said first spacing; and
   a second container contains an automated fluid transfer device.

* * * * *